United States Patent [19]

Leight

[11] 4,434,794
[45] Mar. 6, 1984

[54] DISPOSABLE EAR PLUG

[76] Inventor: Howard S. Leight, 3945 Ridgemont Dr., Malibu, Calif. 90265

[21] Appl. No.: 273,367

[22] Filed: Jun. 15, 1981

[51] Int. Cl.³ ............................................. A61F 11/02
[52] U.S. Cl. .................................................... 128/152
[58] Field of Search ............... 128/118, 151, 152, 270, 128/153, 269; D24/63, 67; 426/134; 215/200; 604/1, 11, 285, 904

[56] References Cited

U.S. PATENT DOCUMENTS

| Re. 29,487 | 12/1977 | Gardner, Jr. | 128/152 |
|---|---|---|---|
| 2,538,339 | 1/1951 | Thomas | 128/152 |
| 2,888,921 | 3/1956 | Nielson et al. | D24/67 |
| 3,352,307 | 11/1967 | Bloxham | 604/1 |
| 3,523,535 | 9/1970 | Croon | 128/285 |
| 4,160,449 | 7/1979 | Wade | 128/152 |

FOREIGN PATENT DOCUMENTS

| 476851 | 9/1915 | France | 128/152 |
|---|---|---|---|
| 832671 | 4/1960 | United Kingdom | 128/151 |

Primary Examiner—Henry J. Recla
Assistant Examiner—Karin Reichle
Attorney, Agent, or Firm—Freilich, Hornbaker, Rosen & Fernandez

[57] ABSTRACT

An ear plug is described, which includes a shell formed of closed cell foam material, with the shell surface having a multiplicity of small bumps that also form the walls of cells which lie at the surface of the shell, whereby to avoid wrinkling when the shell is squeezed into the ear canal. A stem of resilient material lies freely moveable in the shell, and is short so it extends substantially no further than the open end of the shell.

6 Claims, 7 Drawing Figures

DISPOSABLE EAR PLUG

BACKGROUND OF THE INVENTION

One type of simple ear plug includes a body formed of soft material for pressing into the ear canal to block it. Such ear plugs can be constructed by injection molding a foamable material into a die, which forms a foam body with a smooth thin skin on the outside. However, it has been found that when such an ear plug body is pressed into the ear canal, the skin on the plug body does not uniformly contract, so that wrinkles may be created through which sound can pass to reduce the effectivness of the ear plug. Furthermore, when workers handle the ear plugs by grasping them, they sometimes pinch the outer skin which causes it to crack. The ear plug is often provided with a stem extending perhaps a centimeter behind the plug body to aid in installation and removal from the ear. However, the stem must be soft to minimize danger to the wearer, and the soft stem does not help much in pressing the plug body into the ear. An easily constructed ear plug which avoided wrinkling when pressed into the ear canal or cracking when pinched, and which could be easily installed in the ear, would enable more effective ear plugs to be constructed.

SUMMARY OF THE INVENTION

In accordance with one embodiment of the present invention, an ear plug is provided which is rugged and which effectively seals the ear canal against the passage of sound therethrough. The ear plug includes a shell which can be formed of resilient closed cell material, with the outer surface of the shell forming multiple small bumps, these bumps being the walls of cells lying at the surface of the shell. The thin walls of the cells enable the shell to be reduced in diameter when pressed into the ear, without the formation of small wrinkles through which sound can pass. Additionally, when the shell is pinched, the thinness of the cells results in good resistance to cracking of the shell surface. The multiple bumps also provide friction holding of the shell to resist dislodging of the ear plug from the ear canal.

The ear plug includes a stem of about the same length as the shell, and slideable within the shell, to facilitate insertion of the shell into the ear. When the stem is pushed, its front end pushes on the front of the shell, to elongate the shell and thereby reduce its diameter to facilitate shell insertion into the ear canal. When the pushing force stops, the shell can expand. The rear of the shell flares away from the stem, to facilitate grasping of the shell for removal.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
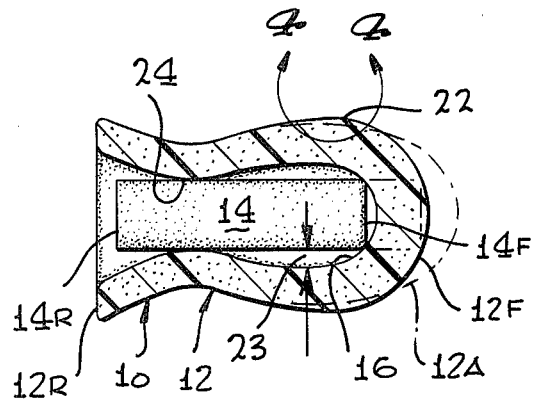
FIG. 1 is a sectional side view of an ear plug constructed in accordance with the present invention.
Figure 2:
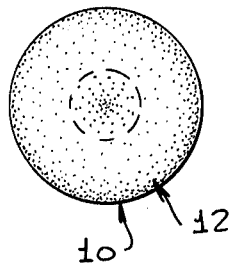
FIG. 2 is a front elevation view of the ear plug of FIG. 1.
Figure 3:
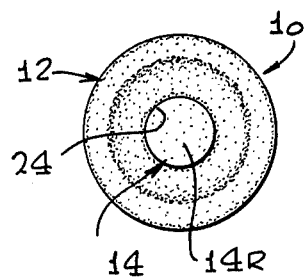
FIG. 3 is a rear elevation view of the ear plug of FIG. 1.
Figure 6:
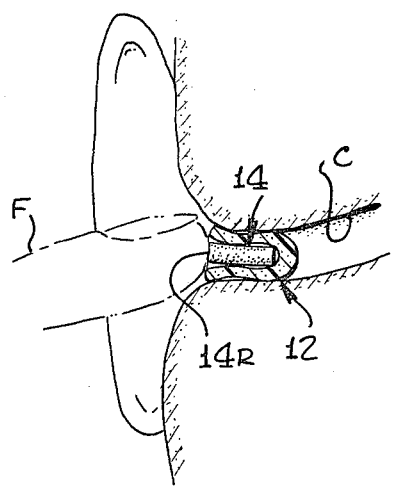
FIG. 6 is a sectional view showing the manner of installation of the ear plug of FIG. 1 in the ear of a person.

FIG. 1 illustrates an ear plug 10 which includes a hollow body or shell 12 and a stem 14 which lies within the cavity 16 of the shell. The shell 12 is constructed of resilient material in the form of a foamed plastic. It can be formed as a closed-cell vinyl foam by processes such as dip molding. The stem 14 is constructed of an elastomeric material which is much stiffer than the material of the shell but which can bend. The ear plug can be utilized by pressing it into the ear canal, as shown in FIG. 6, wherein a finger F of the person presses on the stem 14 to press the shell 12 into the ear canal C.

Figure 4:
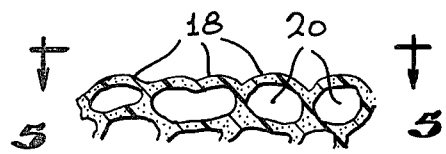
FIG. 4 is an enlarged view of the region 4—4 of FIG. 1.
Figure 5:
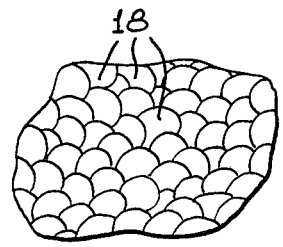
FIG. 5 is a view taken on the line 5—5 of FIG. 4.

FIGS. 4 and 5 are greatly magnified illustrations of a portion of the surface of the shell 12, showing the multiplicity of tiny bumps 18 which appear on the surface. Shells which have been constructed have had bumps with a diameter on the order of magnitude of 0.015 inch. The thin walls of the cells can be easily compressed, and yet the wall of each cell forms part of the walls of adjacent cells. The shell is highly resistant to cracking when pinched, which sometimes occurs during handling of the shell by a worker who is to install it in his ear. It is also found that this closed cell construction, with the bumpy cell walls at the surface of the shell, results in great resistance to the formation of folds in the outer walls of the shell when it is compressed. Any such cracks or folds could provide an airway through which sound can travel into the ear of the wearer, and therefore the shell provides a reliably good seal with the walls of the wearer's ear canal when installed.

The multiple bumps 18 on the outside of the shell surface, also aids in retaining the ear plug shell in the ear canal of the wearer. The multiple bumps increase the friction of the outer shell surface with the walls of the wearer's ear canal, especially since the walls of the wearer's ear can include multiple microscopic irregularities such as those resulting from the irregular surface of the cells of the skin and any small hairs thereon.

The stem 14 is utilized primarily in the installation of the ear plug body or shell 12 in the ear canal, rather than primarily for removal. As mentioned above, a person can install the ear plug in the manner shown in FIG. 6, by pressing on the rear end 14R of the stem. As shown in FIG. 1, pressing on the stem 14, while the periphery of the shell at 22 is held back, causes the front 14F of the stem to press against the front 12F of the shell. This causes the tapered front end of the shell to elongate, as to the position shown at 12A. Such elongation causes the largest diameter portion of the shell at 22, to contract in diameter, so that it more easily moves into the ear canal. Of course, when forward pressure of the stem end 14F is removed, the shell tends to expand and remain tightly sealed in the ear canal. In the course of pressing and releasing the stem 14, its rearward portion slides within the shell, and therefore the stem can be constructed to merely lie within the shell to slide therein, rather than being securely joined to the shell. It may be noted that the shell cavity has a much larger diameter than the stem immediately within the shell location 22, to provide a gap 23 that permits reduction of the shell diameter.

In order to prevent accidental loss of the stem 14, it is constructed so there is a slight interference between it and the walls of a throat 24 formed in the cavity 16 of the shell. The stem and throat 24 can be constructed to the same nominal diameter, and slight irregularities will result in a slight interference fit. The foam material of the shell is very compliant, so that such slight interference fit does not prevent sliding of the stem relative to the shell during forward pressure on the rear of the stem. It would be possible to bond or otherwise attach the forward end 14F of the stem to the forward end of the walls of the cavity 16, but this would add to the expense of manufacture. It is also possible to provide a wide insert beween the stem end 14 F and the shell, but it has been found unnecessary in ear plugs that have been constructed. It may be noted that during forward movement of the stem to elongate the shell and reduce its diameter, the volume of the cavity 16 is reduced. The only slight interference between the stem 14 and the throat 24 of the cavity walls, permits expulsion of air from the cavity, which would otherwise resist elongation of the shell.

The stem 14 is constructed with a length about the same as the length of the shell 14, and in fact has a length somewhat smaller than the length of the shell. FIG. 1 shows that the rear end 14R of the stem does not extend behind the rearward end 12R of the shell. This lack of a rearward extension of the stem, avoids danger to the wearer that could result if the stem extended rearward of the shell so that accidental pressing on such an extending stem might drive it deeply into the ear canal.

In the prior art, stems of very soft resilient material have been utilized which extended rearward of the ear plug body that fit into the ear, to facilitate removal of the ear plug. In the present ear plug, the stem 14 is constructed to be much stiffer, as by forming it of much stiffer resilient material than the very soft material of the shell, to enable the transmittal of pressing forces during the installation of the shell into the ear. A long stem of such stiffer material could be dangerous if it extended further rearwardly. The absence of any stem extending behind the shell, also helps in removing fear from the wearer that the shell might be accidentally driven deep into his ear canal.

Removal of the shell from the ear can be accomplished by the wearer grasping the rear end 12R of the shell and pulling it out. To facilitate such grasping, the rearward end of the shell is constructed so it flares away from the stem 14. By "flare away from the stem", it is meant the opposite sides of the rear end of the shell are not parallel to each other, but instead extend at an angle to each other, with the angle being much less than 180°. This results in a protruding shell portion that can be grasped by the finger tips to remove the shell. In addition, the rearward end 12R of the shell extends beyond the rearward end 14R of the stem, to provide a small region of the shell that can be grasped by the fingertips.

As mentioned above, the stem 14 is constructed of a fairly stiff but resilient material. Ear plugs have been constructed utilizing stems formed of neoprene closed cell foam material. The stem is stiff enough to resist compression along its length, to facilitate insertion of the ear plug, and yet can bend sidewardly. Such slight sideward bending is useful in enabling the entire ear plug to bend slightly to conform to the curvature of the ear canal.

Tests conducted on ear plugs constructed as described above, have shown them effective in reducing sound transmission by between 25 to 30 decibels. This is as good as the most effective available ear plugs which are formed of material which undergoes delayed expansion after being compressed in the hands of the wearer and then installed in the ear canal and kept there until expansion is complete after perhaps ½ to 1½ minutes. The present ear plug has the advantage over such a prior art ear plug of avoiding the need to roll the ear plug in the hands of the wearer for compression which can dirty the ear plug when the wearer has dirty or greasy hands, and of avoiding the need to keep the ear plug pressed in place for the period of perhaps one-half to one and one half minutes before it fully expands. The present ear plug produced greater noise reduction than prior art simple insertion ear plugs that are available.

Figure 7:
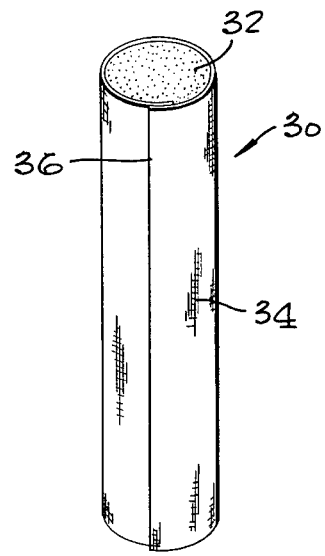
FIG. 7 is a perspective view of an earplug stem constructed in accordance with another embodiment of the invention.

FIG. 7 illustrates another stem 30 which has been found to operate well in the shell 12 of FIG. 1. The stem 30 includes a solid rod 32 of relatively soft and pliable foam material of about the same softness as the shell. It is stiffened by a layer of tape 34 with overlapping ends forming a tube with a thickened strip-shaped portion 36. The tape 34 is a fabric tape that is bonded by adhesive to the rod and that stiffens the rod against column collapse, while allowing the rod to be constructed at low cost. The thickened portion 36 helps prevent loss of the stem from the shell by its slight interference fit in the throat of the shell, although it can slide therein. A large number of stems can be formed by laying a long rod on a long strip of tape, bending the tape around the rod with slight tape overlap, and cutting the resulting shaft into individual stems.

Thus, the invention provides an ear plug which can be constructed at low cost, which can be installed quickly and without requiring procedures that can dirty it, and which is highly effective to the reduction of sound. This is accomplished by utilizing an ear plug shell or body of closed cell foam material, wherein the walls of the cells which lie at the surface of the plug body, form the outside surface of the body with multiple tiny bumps. A stem which aids in inserting the plug body into the ear canal, can have a length substantially no longer than the length of the plug body, so it can be constructed of relatively stiff (compared to the plug body) resilient material, to enable pressing forces on the stem to be transmitted to the front of the body or shell to enable its elongation to help reduce the diameter of the shell. The stem can be slidably received in the shell, at least at a rearward throat area of the shell.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. An ear plug comprising:
    an ear plug body constructed to enable its reception in the ear and having outside walls adapted to directly contact the surface of the ear canal, said plug body constructed of dip-molded closed cell foam material and having a body surface defining said outside walls with a multiplicity of small bumps formed solely by closed cells of said foam material which lie at the surface of said body.

2. The ear plug described in claim 1 wherein:
said plug body has a cavity and a closed front end and open rear end; and including
a stem of resilient material which is stiffer than said body lying in said cavity, said stem being freely slideable with respect to all portions of said body.

3. An ear plug comprising:
a resilient plug body which is hollow to form a cavity, said plug body having a closed front end and an open rear end opening to said cavity enabling its reception in the ear and having outside walls adapted to directly contact the surface of the ear canal;
said plug body is constructed of dip-molded closed cell foam material, with said outside walls of the body defining a multiplicity of small bumps formed solely by closed cells of said form material which lie at the surface of said body;
a stem lying in said hollow body, said stem having a front end lying at the front of said cavity, and said stem having a rearward end extending rearwardly substantially no further than the rear of said plug body;
said stem being freely slideable within at least the rearward portion of said cavity.

4. The ear plug described in claim 3 wherein:
said plug body cavity has a throat portion near the rear end of the body, and the rear walls of said body behind said throat flare out away from said stem by a flare angle of less than 90° to the length of the stem, and the rear of the body is open, whereby to facilitate grasping the body to pull it out of the ear.

5. An ear plug comprising:
a resilient plug body which is hollow and which has a closed front end and an open rear end; and
a stem lying in said hollow body, said stem having a front stem end lying at substantially the front of the inside of said body and a rear stem end extending rearwardly substantially no further than the rear of said hollow plug body;
said stem includes a rod of soft resilient material and a layer of stiffer material than the rod surrounding said rod.

6. An ear plug comprising:
an ear plug body constructed to enable its reception in the ear, said plug body constructed of closed cell foam material and having a body surface with a multiplicity of small bumps which also form the outside walls of some of said closed cells which lie at the surface of said body, said plug body having a cavity and a closed front end and open rear end;
a stem having a front stem end lying in said body adjacent to said front end of said body, and a rear stem end portion extending substantially through said open rear end of said plug body to enable a person to press on the rear of the stem;
said stem including a rod of soft foam material and a layer of material extending around said rod to stiffen it.

* * * * *